United States Patent [19]

Yamaguchi et al.

[11] Patent Number: 4,532,644
[45] Date of Patent: Jul. 30, 1985

[54] X-RAY COMPUTERIZED TOMOGRAPH

[75] Inventors: Keiki Yamaguchi; Tadashi Ogawa; Masayoshi Mitamura; Tooru Shimizu, all of Musashino, Japan

[73] Assignee: Yokogawa Hokushin Electric Corporation, Tokyo, Japan

[21] Appl. No.: 449,144

[22] Filed: Dec. 13, 1982

[30] Foreign Application Priority Data

Oct. 8, 1982 [JP] Japan ............................. 57-177275

[51] Int. Cl.³ ............................................ G03B 41/16
[52] U.S. Cl. ....................................... 378/16; 378/106
[58] Field of Search ................... 378/101, 106, 5, 16, 378/108, 4, 19

[56] References Cited

U.S. PATENT DOCUMENTS 4,048,503  9/1977  Taylor .................................. 378/19
4,051,378  9/1977  Kreppner ............................. 378/16

OTHER PUBLICATIONS

"Transistor Manual", Radio Corp. of America, Harrison, N. J. 1964, pp. 54, 55.

Primary Examiner—Craig E. Church
Attorney, Agent, or Firm—Moonray Kojima

[57] ABSTRACT

A rotate/rotate type X-ray computerized tomograph system employing a single-phase transformer as a high tension voltage supply whereby the secondary voltage of the single phase transformer is rectified and applied across the anode and cathode of an X-ray tube. Such a system, advantageously, is compact and lightweight and employs components which are substantially less costly than those of the prior art.

15 Claims, 11 Drawing Figures

X-RAY COMPUTERIZED TOMOGRAPH

BACKGROUND OF THE INVENTION

1. Field of the Invention

This invention relates to a rotate/rotate type X-ray computerized tomograph apparatus or system, and more particularly to an apparatus or system for obtaining the tomograph of an object being examined by a method wherein high-tension voltage is applied to an X-ray tube so that pulses of X-ray are radiated upon an object being examined and the X-rays that have passed through the object are detected by an X-ray detector and the detected signals are processed by a processor, such as a computer, to produce the tomograph.

2. Description of the Prior Art

Figure 1:
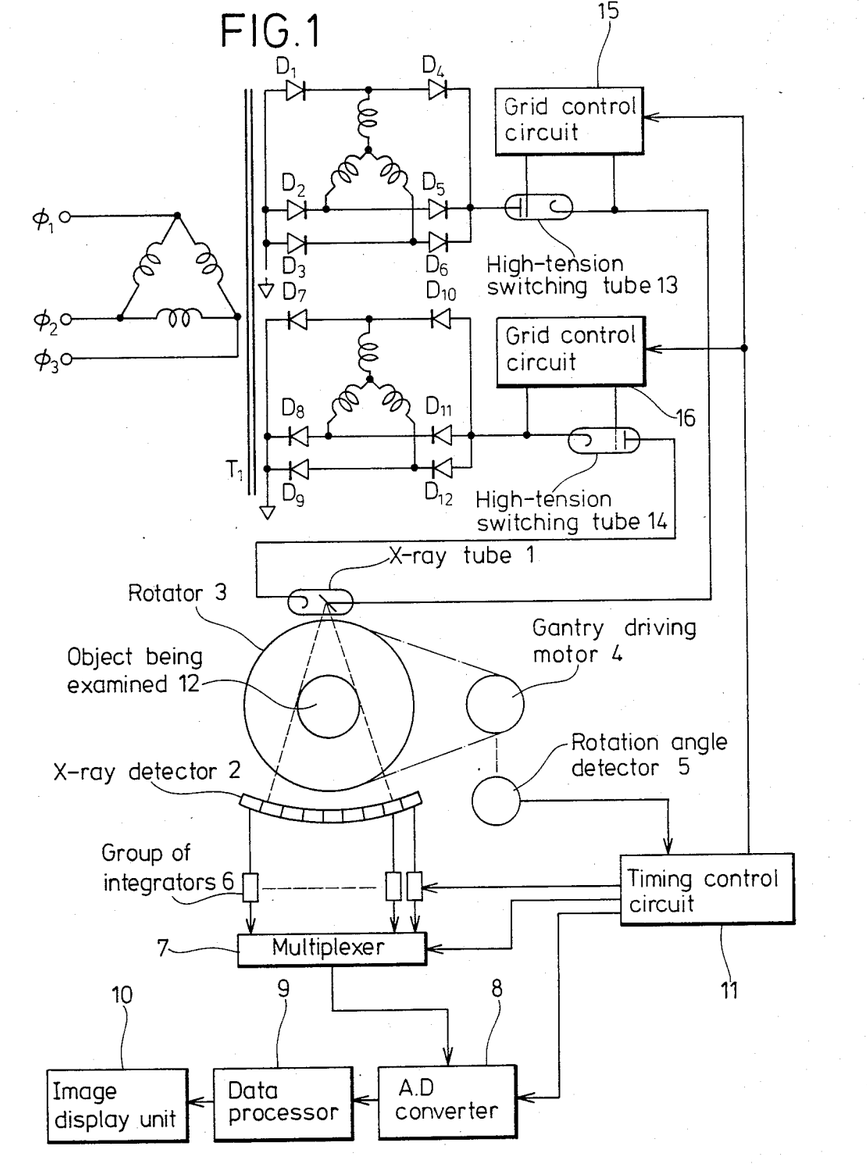
FIG. 1 is a block diagram illustrating a conventional X-ray computerized tomograph system.

A conventional X-ray computerized tomograph system heretofore used is shown in FIG. 1. The system comprises an X-ray tube 1, which outputs X-rays corresponding to voltage applied across its cathode and anode electrodes. The X-ray usually has a pulse shaped wave because voltage applied thereto usually is a pulse shaped wave. An X-ray detector 2 is disposed opposite the X-ray tube 1, with an object 12 being examined disposed therebetween. The tube 1 and detector 2 are movable relative to the object 12. For example, the tube and detector may be rotated about the object 12, such as by means of gantry driving motor 4. The drawing is representational in nature, and intends to show the tube 1 and detector 2 rotating about object 12, by means of a rotator 3. Similarly the object 12 may be rotated with the X-ray tube 1 and detectors held stationary.

X-ray detector 2 is provided with a plurality of detector elements set in an array. Each of the detector elements functions to output current corresponding to the strength of an X-ray incident thereupon after passing through object 12. Rotator 3, to which X-ray tube 1 and detector 2, have been attached, is driven or turned by a gantry driving motor 4 (hereinafter referred to as a motor). A rotation angle detector 5 is connected for detecting the rotation angle of rotator 3 and for providing signals to timing control circuit 11. The timing circuit and rotation detector are known devices, such as described, for example, in U.S. Pat. No. 4,048,503. A group of integrators 6, comprising a plurality of integrators, is connected for integrating currents supplied by each of the elements of the X-ray detector 2. Each integrator is connected to and controlled by timing control circuit 11, described hereinafter, in terms of its integral period so that an integrated value can be obtained on a pulse basis from pulse current inputted successively by X-ray detector 2, at predetermined periods. The integrators are connected to a multiplexer 7, which selects the output of each integrator and transmits the output to a next level. AD converter 8 is connected to the multiplexer 7, for converting an analog signal supplied by multiplexer 7, into a digital signal, and connected to data processor 9 which processes the digital output thereof.

The multiplexer 7 and AD conveerter 8 are connected also to timing control circuit 11. Data processor 9, such as a computer, is connected for receiving signals from converter 8 and for transmitting processed signals to image display unit 10. The processor 9 processes the signal data which is based on the intensity of the X-rays that have passed through the object being examined and transmitted via AD converter 8, thereby to obtain a tomograph. Image display unit 10, which may be a cathode ray tube, displays the resulting tomographs.

Timing control circuit 11, which is connected at its input to detector 5, and at its output to integrators 6, multiplexer 7, converter 8, grid control circuits 15 and 16, functions to regulate the timing of various components upon receiving signals from rotation angle detector 5 in a manner to be hereinafter explained in greater detail. The supply circuit comprises high tension switching tubes 13 and 14, which may be tetrode type tubes; grid control circuits 15 and 16; a Y-connected three-phase transformer $T_1$; and rectifiers $D_1$–$D_{12}$, connected to each other in the manner depicted and connected to X-ray tube 1, to supply high-tension voltage thereto.

The circuitry and components of each of the components set forth in FIG. 1 and other figures in the drawing, are known. These are generally available off the shelf commercially. For example, the AD converter is well known, and can be obtained readily on the market and installed with only the description given herein, and operated to perform the functions set forth herein.

Figure 3:
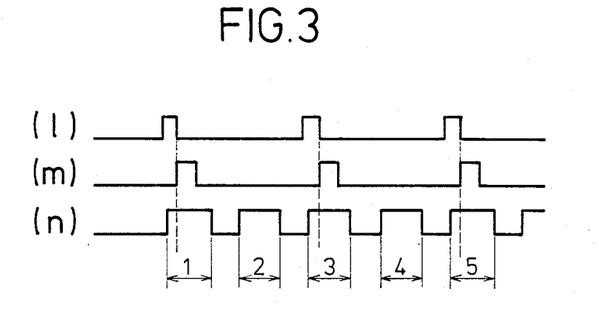
FIG. 3 is a time chart illustrating the operation of the apparatus of FIG. 1.

Operation of the conventional X-ray computerized tomograph apparatus of FIG. 1, will now be explained with reference to FIG. 3. The three phase transformer $T_1$ and the rectifiers $D_1$–$D_{12}$ make available d.c. voltage, with little voltage regulation, and the d.c. voltage obtained, is applied as high tension voltage to X-ray tube 1, through high tension switching tubes 13,14. FIG. 3 is a time chart wherein (l), (m) and (n) illustrate the action of the components shown in FIG. 1. In FIG. 3, waveform (l) is the output of rotation angle detector 5; waveform (m) is the X-ray pulse irradiated from the X-ray tube 1; and waveform (n) is the behavior of integrator 6. Rotator 3 is suitably turned by motor 4 and its rotation angle is detected by rotation angle detector 5 and a pulse signal (l) is outputted by detector 5 to timing control circuit 11 at every predetermined angle (e.g. every 1°).

As shown in FIG. 1, timing control circuit 11, for example, allows grid control circuits 15,16 to operate syncronously with the trailing edges of pulse (l) thereby to apply a high tension pulse to X-ray tube 1, so that the pulse (m) of X-ray tube 1 is irradiated onto the object 12. The irradiated X-ray pulse (m) passes through object 12, being examined, and is detected by X-ray detector 2. The current measured by X-ray detector 2 shows a pulse waveform synchronized with what is shown by waveform (m) in FIG. 3 and integrator 6 integrates the current in each of waveform (n) periods (1), (3) and (5), to convert the quantity of transmitted X-ray into a voltage value.

On the other hand, for correcting for circuit error factors and the like, integrator 6 also carries on integral control action in periods (2) and (4) shown by waveform (n) in FIG. 3. The integral values obtained in the apparatus in these periods (2) and (4) are the ones when X-ray input is zero. This procedure is often termed zero signal correction. By making equal the time intervals for periods (2) and (4) and those of periods (1) (3) and (5) the zero current variation of an integrator and the like will be corrected, if the values obtained in periods (2) and (4), which represent zero current correction factor, are subtracted from the data signal obtained during periods (1), (3) and (5), that is the signals from the X-ray detector representing the signal transmitted through the object. The integrator 6 is reset during the periods between (1) and (2) and (3). As mentioned, the integrator alternatively repeats integration at the time of X-ray irradiation, resets, zero current correction integration, resets, syncronous with the timing of the pulse shaped high tension voltage applied to the X-ray tube, whereby a tomogram is displayed on the image display unit 10 from the data signal tansmitted through AD converter 8 and data processor 9.

However, the conventional X-ray computerized tomograph system, such as depicted in FIG. 1, has the following deficiencies or disadvantages.

The high tension voltage generator employs a three phase transformer to obtain a semi-d.c. output at ±60 kV, so that the generator is likely to be complicated in construction, large sized and costly. The only voltage supply, including a transformer, of the computerized tomograph system currently sold on the market, weighs about 1.3 tons, and is therefore not readily movable.

The prior computerized tomograph system is also very expensive because it requires high tension voltage switching tubes and grid control circuits provided with high tension voltage insulating functions.

Figure 4:
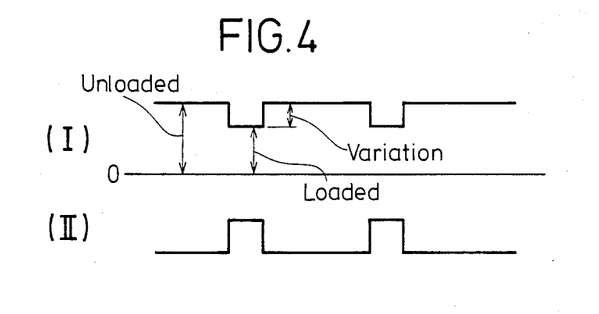
FIG. 4 is a diagram of load variations in the apparatus of FIG. 1.

Also, in the prior system, even under a no-load condition voltage rises, thus requiring the components to have greater dielectric strength which entails large and expensive components. FIG. 4(I) is a diagram indicating the waveform of output voltage in the loaded and unloaded conditions, as applied by rectifiers $D_4$–$D_{12}$ (of FIG. 1) as high tension voltage generators. FIG. 4(II) shows the waveform of current flowing into X-ray tube 1.

As shown in FIG. 4, the high tension voltage output in the high tension voltage generator (shown in FIG. 1) fluctuates because the load current (which is the cube of the current) changes. Accordingly, when the desired high tension voltage is supplied to the load, the voltage under a no-load condition rises (see FIG. 4.(I)), thus requiring the components of the high tension voltage generator, including the transformer, to have high dielectric strength, and thus making the system largesized and expensive. For this reason, in the prior art, the X-ray tube voltage has been limited to approximately 120 kV.

SUMMARY OF THE INVENTION

Accordingly, an object of the invention is to eliminate and overcome the aforementioned and other deficiencies and disadvantages of the prior art.

Another object is to simplify and reduce in size, complexity and cost, the power supply for the X-ray source.

A further object is to eliminate costly high tension switching tubes and grid control circuits which require high tension voltage insulators.

A still further object is to reduce the dielectric strength requirements of the power source components, and on the other hand, to expand the voltage limitations of the X-ray source.

Another object is to accomplish the foregoing objects while still retaining the other advantages of such apparatus, such as good stability of X-rays radiated from X-ray tubes.

The foregoing and other objects of the invention are attained in an X-ray computerized tomograph system comprising an X-ray tube, a power source for powering the X-ray tube, a plurality of detectors which together with the X-ray tube are movable relative to an object to be examined, and a processing circuit for taking signals from the detector and processing them relative to the position and timing of the X-ray tube output and detector relative to the object, to thereby produce a tomograph of the object being examined. Advantageously, the power source is a single phase transformer having a primary winding and secondary winding with rectifier means whereby the rectified voltage is supplied to the X-ray tube thereby enabling simplification of the power source and system.

In one embodiment, the rectifier means is a half wave rectifier and a phase lock loop circuit is connected between the primary winding and a circuit which drives a motor to move the X-ray tube and detector relative to the object.

In another embodiment, the rectifier means is a full wave rectifier, with the phase lock loop circuit connected as for the half-wave rectifier.

A further embodiment employs the phase lock loop circuit and a rectifier and capacitor connected in series with the secondary winding, with the X-ray tube being connected in parallel to the rectifier.

In another embodiment, the X-ray tube is a triode tube having anode, cathode and grid electrodes, with the anode and cathode being connected across the rectified secondary voltage, and circuitry is provided for applying a signal to the grid which is geared to the peak of applied voltage, such circuitry comprising a phase locked loop circuit, phase shifter, and grid control circuit.

In yet another embodiment, to prevent deflected magnetized current in the primary winding, a diode or thyrister and resistor combination, is connected to the primary winding of the transformer. Where voltage regulation is present, similar deflected magnetized current may be prevented from occuring in the regulator winding by connected a diode or thyristor and resistor combination to the voltage regulator transformer winding.

The different embodiments may be used together with a circuit which corrects the output signals for zero current factors and errors which exist in the circuit, that is for, such factors as noise, etc, which may exist in the circuit without application of input current. Such a zero signal correction circuit may be one or more of those disclosed in Ser. No. 444,329 filed on Nov. 24, 1982, and assigned to the same assignee as hereof, the copending application by reference being made a part hereof.

The instant invention advantageously simplifies the circuitry and apparatus, enables use of increased voltages, decreases dielectric strength requirements of components used herein, and produces other advantages, such as reduces cost and size and complexity.

A feature of the invention is the use in a X-ray computerized tomograph system of a single phase transformer with rectifier means connected to its secondary winding for application of rectified voltage to the X-ray tube used therein, and a phase locked loop circuit connected between the primary winding and a motor which moves the X-ray source relative to the object being examined for syncronous movement with the rectified output.

A further feature is the use of half-wave or full-wave rectifiers as the rectifier means.

A further feature is the connection of a rectifier and capacitor in series across the secondary winding and connection of the X-ray tube in parallel to the rectifier.

A still further feature is the use of an X-ray triode tube having anode, cathode and grid electrodes, with the anode and cathode being connected across the rectifier means, and synchronizing circuitry connected to the primary winding for applying signals to the grid.

Another feature is the use in the primary winding of the single phase transformer of a diode or thyristor and resistor combination to prevent deflected magnetized current.

A still further feature is the use in a voltage regulating transformer of a diode or thyristor and resistor combination, to prevent deflected magnetized current.

Another feature is the combination of any one or more of the above features with a circuit for making zero current correction.

DESCRIPTION OF PREFERRED EMBODIMENTS

Figure 2:
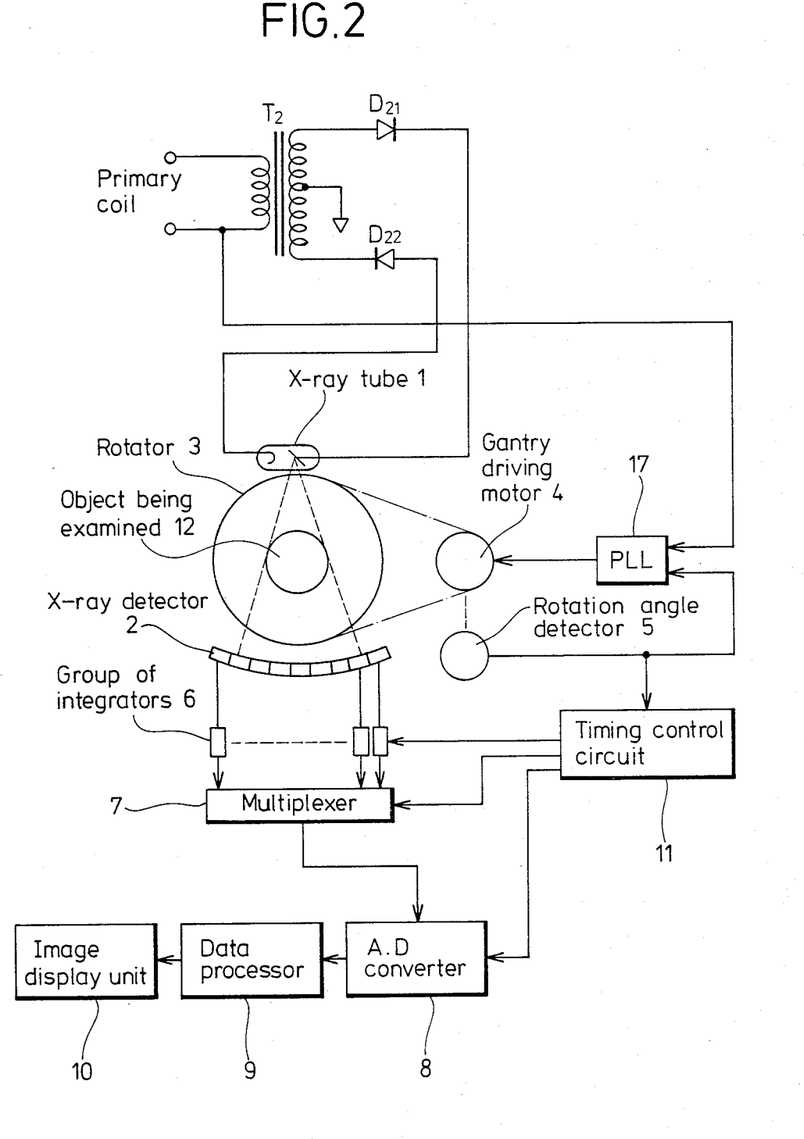
FIG. 2 is a block diagram of an illustrative embodiment of the invention.

Referring now to FIG. 2, which depicts an illustrative embodiment of the invention, components 1–11, are similar to those depicted in FIG. 1, and hence the description thereof is omitted for sake of clarity and brevity of description. The main difference between the system of FIG. 1, and the X-ray computerized tomograph system of FIG. 2, which is an illustrative embodiment of the invention, comprises the use of a single phase transformer $T_2$, as the power source transformer, and two rectifiers $D_{21}$ and $D_{22}$, and a phase locked loop circuit 17 (hereinafter referred to as PLL) for comparing a signal supplied by the rotation angle detector 5 with the frequency of a commercial voltage supply in terms of phase to allow the rotator 3 (by means of gantry driving motor 4) to which the X-ray tube 1 and the X-ray detector have been attached, for example, to rotate in synchronism with the frequency of the commercial supply. The phase locked loop circuit is known, such as described, for example, in Handbook of Electronic Circuit Design Analysis, by Harry Thomas, P.281, Reston Publishing Co., Inc., Reston, VA, 1972. Of course a non-commercial voltage supply can be used.

Figure 5:
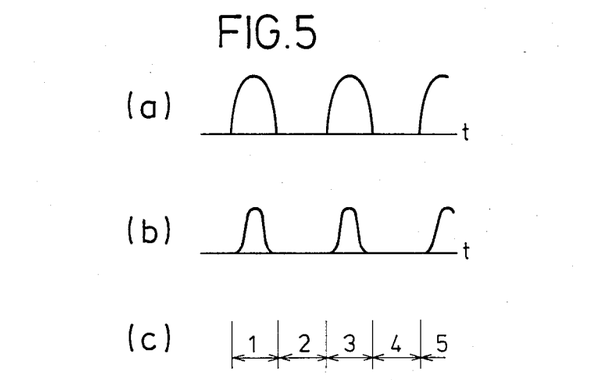
FIG. 5 is a time chart illustrating the operation of the embodiment of FIG. 2.

FIG. 5 is a time chart illustrating the action of certain components of the apparatus of FIG. 2. In FIG. 5, line (a) shows the waveform of a high tension voltage as processed through half-wave rectification and applied across the anode and cathode of the X-ray tube 1. Line (b) indicates the pulse waveform of X-ray radiated from X-ray tube 1. Line (c) is a diagram explanatory of the operating periods of group of integrators 6.

The voltage supplied by a commercial voltage supply, for example, is applied to the primary winding of the single phase transformer $T_2$ in the X-ray computerized tomograph of FIG. 2. The desired high tension voltage is induced in the secondary winding of the transformer $T_2$ and processed through half wave rectifiers $D_{21}$ and $D_{22}$ to supply a half wave rectified dc voltage. The voltage of waveform shown in FIG. 5(a) is applied across the anode and cathode of X-ray tube 1. Although each of rectifiers $D_{21}$ and $D_{22}$ shown in FIG. 2, is defined as a single element, a plurality of elements connected in series may be used for rectification so that dielectric strength is provided.

Since the radiation quantities of X-rays radiated from X-ray tube 1, are proportional to about a cube of the tube voltage, the radiation output has a pulse wave form, such as shown in FIG. 5(b).

On the other hand, as described earlier, rotator 3 is rotated synchronously with frequency of the commercial voltage supply, because of the action of PLL 17, whereas a pulse wave of X-ray synchronous with the frequency of the commerical supply, is also radiated from X-ray tube 1.

The group of integrators 6 carries out integral control action in each of the periods (1), (3) and (5) in FIG. 5(c), thus converting the X-ray quantity, inputted during each period, into a voltage value, and integrating the current in each of the periods (2), and (4) shown in FIG. 5(c), at a zero current level, when the X-ray is not irradiated. The data thus obtained from the periods (1), (3) and (5) are processed for zero current correction, (that is the zero current correction obtained from periods (2) and (4) are subtracted from the signal obtained in periods (1), (3) and (5), by a circuit such as shown in the above mentioned co-pending application Ser. No. 444,329) and then converted into images by data processor 9, which images are then displayed on image display unit 10, as a tomogram. Instead of zero correction by means of a data processor, such as processor 9, analog zero current correction may be carried out by each integrator, such as referred to in the above mentioned copending application Ser. No. 444,329.

Figure 6:
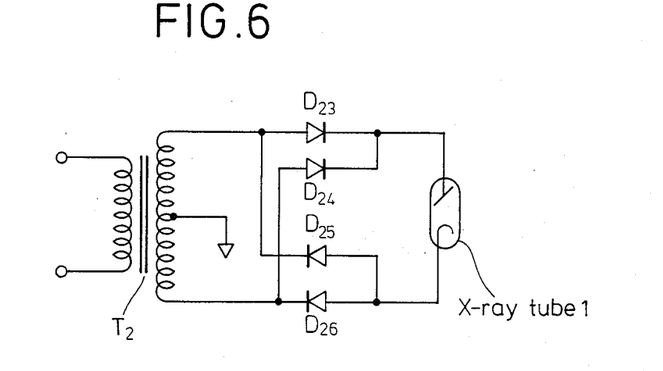
FIGS. 6, 7 and 8, are diagrams of other illustrative embodiments of the invention, with components other than the power source, such as shown in FIG. 2, being deleted for sake of clarity.

FIG. 6 is a diagram illustrating another example of the instant invention, wherein a single phase transformer $T_2$, rectifiers $D_{23}$–$D_{26}$ and X-ray tube 1 only are depicted for sake of clarity and brevity of description. Other components and connections of these components to the other components are the same as those shown in FIG. 2, and it is to be understood that these components depicted in FIG. 6 are to be used with those other components depicted in FIG. 2, and that such combination of elements is intended hereat. The same consideration will apply for the embodiments shown in FIGS. 6, 7, 8, 10 and 11. The description of the other elements and components and connections of FIG. 2 are omitted in these figures and hereat for the sake of simplifying description.

In the apparatus shown in FIG. 6, a commercial voltage supply is applied to the primary winding of single phase transformer $T_2$ as in the case of the embodiment of FIG. 2, and a pulse wave of high tension voltage, processed through full wave rectification, is supplied to X-ray tube 1. Accordingly, the pulse waves of X-rays, twice as many as those in FIG. 5(c), are irradiated from X-ray tube 1. When the full wave rectification of FIG. 6 is employed, the integral period for the zero current correction in periods (2) and (4) in FIG. 5(c) is not removed. In this case, however, zero integration, in place of zero current correction, on a waveform basis is carried out once at the beginning of the X-ray scanning, in order to obtain zero current correction factor and then the zero current correction factor is substracted from the data obtained for each instance of X-ray irradiation to produce an output signal truly representative of the X-ray irradiation of the object. By using zero current integration, that is obtaining a zero current correction factor at the beginning of each scan, rather than between each pulse of scan, and applying the factor for correction to each scan, advantageously, the number of times the correction factor is obtained is reduced. Copending application Ser. No. 444,329 discloses such a zero current integration circuit, and may be used herein.

Figure 7:
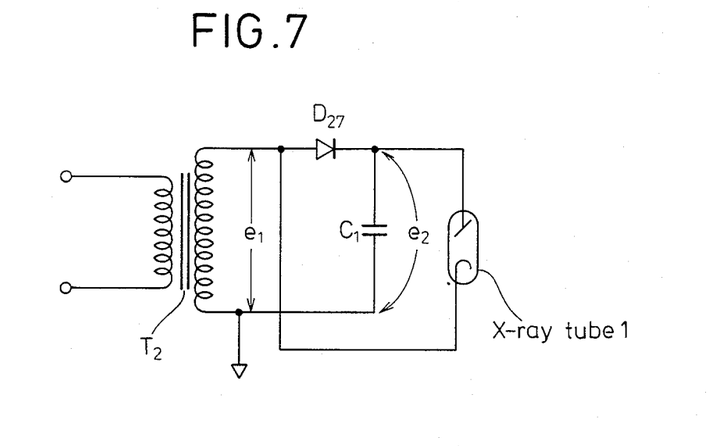

FIG. 7 is a diagram illustrating another embodiment of the instant invention, wherein, as in FIG. 6, only a single phase transformer $T_2$, rectifier $D_{27}$, capacitor $C_1$ and X-ray tube 1, are shown. The remainder of the X-ray tomograph system is the same as in FIG. 2, and this description is understood to include such other components. In FIG. 7, rectifier $D_{27}$ and capacitor $C_1$ connected to each other in series circuit, are connected to the secondary winding of single phase transformer $T_2$, in the manner depicted. X-ray tube 1, is connected to rectifier $D_{27}$ in parallel in such a manner that tube is opposite in polarity to the rectifier $D_{27}$. In FIG. 7, when a commercial voltage supply, for example, is applied to the primary winding of transformer $T_2$, voltage is induced in secondary winding thereof. By action of the rectifier $D_{27}$ and capacitor $C_1$, capacitor $C_1$ is charged with positive d.c. voltage $e_2$ and processed with peak rectification for the anode of X-ray tube 1. On the other hand, a.c. voltage $e_1$, induced in the secondary winding of transformer $T_2$, is applied to the cathode of X-ray tube 1. Accordingly, the positive voltage ($e_2-e_1$) is always applied across the anode and cathode of X-ray tube 1 and an X-ray is irradiated when the voltage difference becomes almost maximum.

As has been given by the above description, the X-ray computerized tomograph system illustrated in FIGS. 2, 6 and 7 produce the following advantageous results. (It is to be understood that the other components of FIG. 2 are employed with the components shown in FIGS. 6 and 7).

By use of a single phase transformer, the number of elements for use in a high tension voltage generator, can be minimized in comparison to the generator of the prior art. In addition, the instant invention is compact and inexpensive. The weight of a voltage supply, including a transformer, according to the instant invention can be reduced, for example, from about 1.3 tons to about 0.4 ton.

Expensive high tension switching tubes and grid control circuits are eliminated and are unnecessary.

As shown in FIG. 4, high tension voltage, in the conventional prior art X-ray computerized tomograph system, is affected by load fluctuations. However, the instant invention is not substantially affected by load fluctuations, since rectified voltage is always applied to the load. The eficiency of the X-ray tube is greatly increased because the peak tube voltage of the X-ray tube, may be set at a higher level.

As mentioned, the embodiments of FIGS. 2, 6 and 7 have proven that the aforementioned advantages and results are obtainable. The waveform of the X-ray pulse radiated from the X-ray tube 1 is shown in FIG. 5(b). On the other hand, the X-ray detector in the X-ray computerized tomograph apparatus, measures X-ray pulses that have passed through an object being examined, on a pulse wave basis, and the computer is used to process data based on the measured value so as to obtain the tomogram. It is desired in an X-ray computerized tomograph system, that the time required for measuring the intensity of an X-ray be as short as possible, because a tomograph must be obtained at a high rate of speed. In view of this consideration, the waveform of the X-ray pulse shown in FIG. 5(b) indicates some smoothness in a portion close to its cutoff point, with a large width pulse. A more sharply defined pulse would be desirable and useful.

Figure 8:
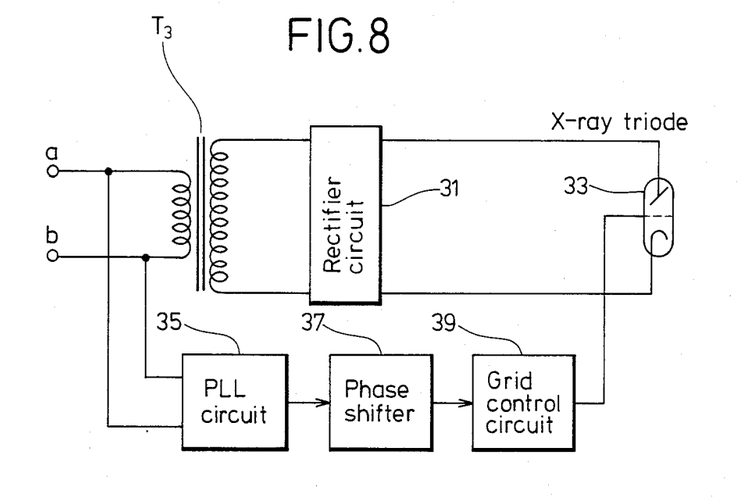

FIG. 8 illustrates an apparatus which, advantageously, is capable of producing an X-ray pulse with a sharp waveform, while the other main effects obtained from the embodiments of FIGS. 2, 6 and 7, are maintained, such as for example, compactness and lightweight components.

The illustrative embodiment of FIG. 8 comprises a single phase transformer $T_3$, which is similar to those described in FIGS. 2, 6 and 7, and a rectifier circuit 31 (which may contain half-wave or full wave rectifier configuration) X-ray triode tube 33 (which is different from the X-ray tube shown in FIGS. 2, 6 and 7 in that an added grid electrode is used). Secondary voltage from single phase transformer $T_3$ is rectified by the rectifier circuit 31 and applied across the anode and cathode electrodes of X-ray triode 33. Also provided is a phase locked loop circuit 35 (hereinafter referred to as PLL) and is similar to the phase locked loop 17 shown in FIG. 2 connected to the primary winding of the transformer $T_3$, for supplying a signal with a frequency corresponding to the frequency of the a.c. voltage applied to the primary winding. For instance, when the input frequency of PLL circuit 35 is assumed to be $f_1$, a signal having a frequency (n) ($f_1$) is supplied. PLL circuit 35 is similar to the PLL circuit 17 illustrated in FIG. 2. PLL circuit 17 and PLL circuit 35 may be incorporated into one for common use. Referring again to FIG. 8, there are shown a phase shifter 37 connected to PLL circuit 35 and to grid control circuit 39. The phase shifter is known, such as shown, for example, in *Pulse and Digital Circuit,* by Jacob Millman and Herbert TAub, P. 498–99, McGraw Hill, 1956. The grid control circuit is known also, such as shown, for example, in U.S. Pat. No. 4,168,436. The phase shifter 37 is capable of suitably shifting the phase of the output signal applied from PLL circuit 35 and transmitting the phase shifted signal to grid control circuit 39. Grid control circuit 39, which is connected to the grid electrode of X-ray tube 33, introduces the phase shifted signal supplied by phase shifter 37, and based on that signal, applies a pulse signal to the gride electrode of X-ray triode 33.

The operation of the embodiment of FIG. 8 is as follows. AC voltage is applied across the terminals a,b of the primary winding of single phase transformer $T_3$. The a.c. voltage is normally supplied from a commercial voltage supply, although non-commercial voltages source can also be used. A predetermined high tension voltage is induced the secondary winding of the transformer $T_3$ and the resulting high tension voltage is rectified by rectifier circuit 31, to become a d.c. voltage with a pulse waveform. As mentioned, either a half-wave or full wave rectifier circuit may be used in rectifier circuit 31, and will perform equally as well and attain the object of this invention. However, the description herein is given in terms of a full wave rectification for sake of convenience.

Figure 9:
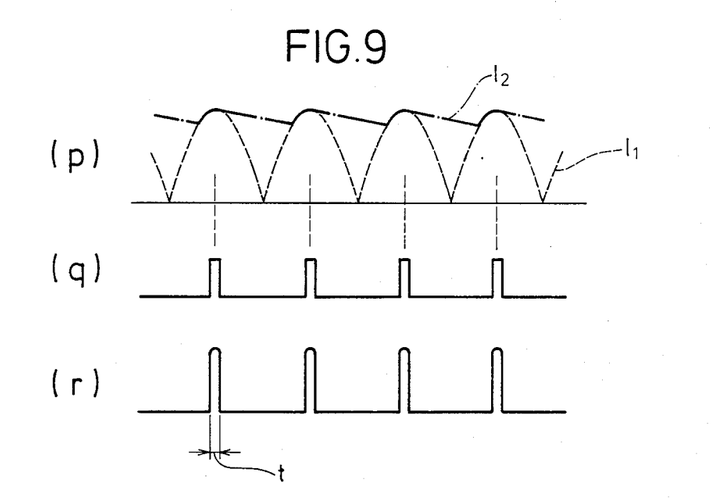
FIG. 9 is a time chart illustrating the operation of the embodiment of FIG. 8.

Referring now to FIG. 9, the waveform processed through full wave rectification of circuit 31, is shown by dotted line $l_1$ in FIG. 9(p). The connection of rectifier circuit 31 with X-ray triode 33 is normally made through a high tension cable (not shown) and, depending on the capacity of the high tension cable, the waveform of the voltage applied across the anode and cathode electrodes of X-ray triode 33 conforms to a dotted chain line l₂ shown in FIG. 9(p). Needless to say, the present invention is applicable to the waveform of voltage to be applied to X-ray triode 33 shown by either dotted line l₁ or dotted chain line l₂ in FIG. 9(p).

On the other hand, PLL circuit 35 is also concurrently sending a signal having a frequency corresponding to the frequency of the a.c. voltage of transformer $T_3$ and, when the single phase transformer $T_3$ outputs an a.c. signal with a frequency, for example, of 50 Hz, the output signal from PLL circuit 35 is allowed to have a frequency of 50 Hz. In FIG. 8, although the primary voltage of the transformer $T_3$ is introduced as the input signal of PLL circuit 35, it may be introduced from a secondary circuit. However, since the secondary side comprises a high tension circuit and must be converted into what has low voltage, a.c. signal is normally introduced into the PLL circuit 35 from the primary circuit of the transformer $T_3$.

A signal with a frequency corresponding to the frequency of the a.c. supply is outputted from PLL circuit 35. Thus, the phase of the output signal produced by PLL circuit 35 can be freely adjusted by phase shifter 37. Accordingly, a pulse signal with the phase shown in FIG. 9(g) can be obtained as the output of grid control circuit 39. In other words, by regulating phase shifter 37, pulse signal generated from the grid control circuit 39 can be synchronized with the peak value of rectified voltage applied across the anode and cathode electrodes of the X-ray triode 33, in terms of the phase of the pulse signal. This relation is indicated in FIG. 9(p) and 9(g). Since the pulse voltage is applied to the grid electrode of X-ray tube 33, when the rectified voltage applied across the anode and cathode electrodes of X-ray triode 33 reaches its peak, a pulse X-ray shown in FIG. 9(r) is radiated from X-ray triode 33.

The embodiment of FIG. 8 produces the following advantages and effects. Pulse voltage is applied to the grid electrode of X-ray triode 33 according to the peak of rectified voltage applied across the anode and cathode electrodes of the X-ray triode 33, so that the X-ray being radiated is free from the effects of ripple fequency of the high-tension supply. Thus, the X-ray output is stable and substantially noise free.

The time for measuring the X-ray can be shortened and response to image display, can be quickened because a sharp X-ray pulse, such as shown in FIG. 9(r), which is different from that shown in FIG. 5(b), is radiated.

Since single phase transformer can be used as the high tension voltage supply, the supply source is compact and lightweight, as in the embodiments of FIGS. 2,6 and 7.

As previously discussed, pulse voltage is applied to the grid electrode of the X-ray triode 33, synchronized with the peak rectified voltage to be applied to the anode and cathode electrodes of the X-ray triode 33. However, the application of such voltage need only be substantially synchronized with the peak for the present invention to attain its objects. The voltage need not necessarily be applied exactly at the peak.

The above description is applicable to full-wave rectifiers being used in the rectifier circuit 31. In the case half-wave rectifiers are used in rectifier circuit 31, the pulse wave shown in FIG. 9(p) occurs every second time and a pulse signal is applied to the grid electrode every time the peak of the pulse wave occurs.

The present invention also employs circuitry to reduce the ripple frequency of the rectified voltage, such as, for example, by connecting a capacitor (not shown) to the output terminal of the rectifier circuit 31, in order to provide allowance for the timing of the pulse signal to be applied to the grid electrode.

According to the description of FIG. 8, PLL circuit 35, phase shifter 37 and grid control circuit 39 are separately constructed. However, any component construction, such as using multiple circuits on a single chip, etc, will serve the object of the invention, as far as the construction can fulfill the functions of these circuits.

Also, the zero current correction circuits described above for the other embodiments and shown for example in copending application Ser. No. 444,329, may be used in connection with these embodiments.

When a half-wave rectifier circuit is connected to the secondary winding of the single phase transformer as shown in FIGS. 2,6,7, or as used in the rectifier circuit in FIG. 8, deflecting magnetized current will tend to flow into the single phase transformer. Such deflecing magnetized current should be prevented from flowing because it tends to reduce the power factor and deteriorates the efficiency of the transformer and of the system.

Figure 10:
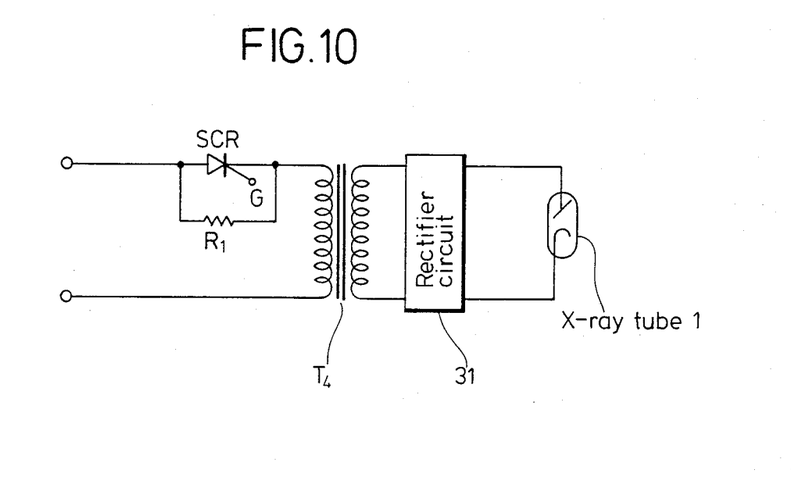
FIGS. 10 and 11 are diagrams illustrating devices for preventing generation of deflecting magnetized current.

FIG. 10 is a diagram illustrating a device for preventing the discussed deflecting magnetized current from flowing into the transformer, and may be used together with any of the embodiments shown in FIGS. 2,6,7,8. The prevention circuit comprises a thyristor SCR and a resistor $R_1$ connected together in parallel, and connected to the primary winding of the single phase transformer $T_4$ in the manner depicted. Other elements depicted in FIG. 10 are shown generally as rectifier circuit 31 and X-ray tube 1. With the construction shown in FIG. 10, single phase transformer $T_4$ in its position half period operates almost in the same manner as when it does not have a thyristor-resistor combination connected in parallel. On the other hand, in the negative half period, although the thyristor operates in the opposite direction, current flows through the resistor $R_1$. When a large deflecting magnetized current is about to flow, the primary voltage of transformer $T_4$ is reduced because of resistor $R_1$, so that the deflecting magnetized current is affected and decreased, or prevented from flowing.

According to the embodiment shown in FIG. 10, because the thyristor SCR may also be used as a supply switch for the X-ray computerized tomograph system as a whole, the ON and OFF conditions of the supply source can be effectively controlled in terms of phase by applying a trigger signal to the gate G of the thyristor SCR with optimum timing.

Since the range of voltage applied to X-ray tube 1 is restricted in an X-ray computerized tomograph system, a voltage regulator is normally installed for voltage regulating purposes. On the other hand, because the primary winding of single phase transformer $T_4$ in the apparatus shown in FIG. 10 is a kind of half wave rectifier circuit, the deflected magnetized current is permitted to flow in the voltage regulator.

Figure 11:
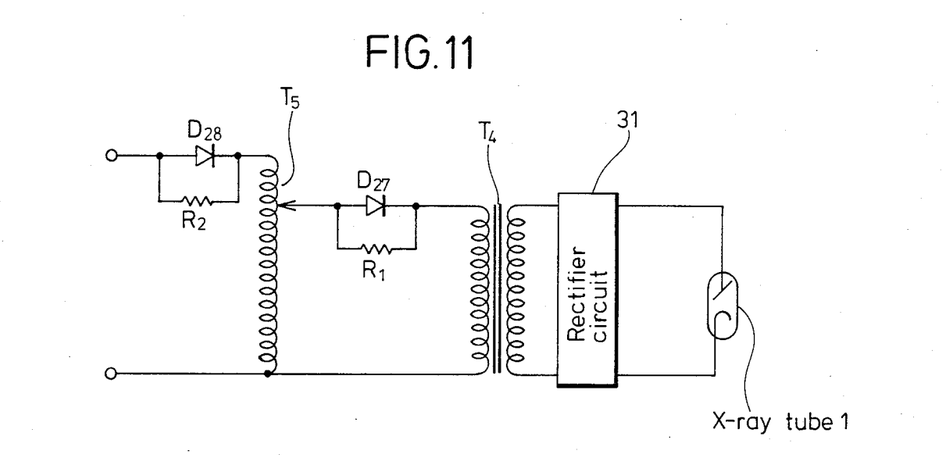

FIG. 11 depicts voltage regulator $T_5$ for voltage regulation and device comprising diode $D_{28}$ and resistor $R_2$ connected to the regulator transformer $T_5$ for preventing deflecting magnetized current from flowing into the regulating circuit $T_5$. The prevention circuit comprising diode $D_{27}$ and resistor $R_1$, is connected across the primary winding of transformer T₄ in the same manner as in FIG. 10 and operates in the same manner as in FIG. 10, to prevent defecting magnetized current in the transformer T₄. Also shown are rectifier circuit 31 and X-ray tube 1, with the remainder of the circuits of FIGS. 2,6,7 and 8 not shown for brevity and simplicity of description. The diodes $D_{27}$ and $D_{28}$ may be thyristors, such as the SCR used in FIG. 10. The operation of the diode 27/resistor $R_2$ combination is the same as for the preventing circuit in FIG. 10. The circuitry involving the voltage regulator, and deflecting magnetized current preventor therefor, may be used in connection with the embodiments of FIGS. 2,6,7 and 8.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. An X-ray computerized tomograph system comprising an X-ray tube having at least an anode and a cathode electrodes for producing pulse wave X-rays according to pulse wave voltages having a predetermined period, applied across said anode and said cathode electrodes; an X-ray detector facing said X-ray tube with an object being examined disposed therebetween, for producing a data signal representing the X-ray signals transmitted through said object; means for rotating said X-ray detector and said X-ray tube; means for detecting rotational position of said object relative to said X-ray tube and said X-ray detector; phase locked loop means responsive to the detected result of said rotational position and the frequency of the input voltage supply, for proportionally syncronizing the rotating movement of said X-ray tube and X-ray with said frequency of said input voltage supply; means for integrating the output of said X-ray detector syncronously with said pulse way X-rays; means for forming a tomogram of said object on the basis of said data signal produced by said X-ray detector; an image display unit for displaying said tomogram; a single phase transformer having primary winding and secondary winding, said primary winding being connectable to an input voltage supply having a selected frequency; and rectifier means connected to said secondary winding to produce a secondary voltage having said selected frequency which is rectified and used as said pulse wave voltage by said X-ray tube to produce at least one said pulse wave X-ray during each cycle of said selected frequency, wherein said pulse wave X-ray is substantially in phase with said rotation of said X-ray tube and said X-ray detector.

2. The system of claim 1, wherein said rectifier means is a half wave rectifier.

3. The system of claim 1, wherein said rectifier means is a full wave rectifier.

4. The system of claim 1, wherein said rectifier means comprises a rectifier and a capacitor connected in series circuit across said secondary winding of said transformer, and said X-ray tube is connected in parallel circuit across said rectifier.

5. The system of claim 1, wherein said X-ray tube is a triode comprising anode, cathode and grid electrodes, wherein the rectified voltage from said rectifier means is applied across said anode and said cathode electrodes; and wherein said phase locked loop means applies a pulse signal to said grid electrode in conformity with substantially the peak value of rectified voltage applied across said anode and cathode electrodes.

6. The system of claim 5, wherein said phase locked loop means applies a signal to said grid electrode comprises a phase locked loop circuit for producing a signal with a frequency corresponding to the selected frequency of the a.c. signal in said single phase transformer, a phase shifter for shifting the phase of the output signal of said phase locked loop circuit, and a grid control circuit for applying a pulse signal to said grid electrode on the basis of the signal produced by said phase shifter.

7. In an X-ray computerized tomograph system comprising
an X-ray source;
a power source connected to said X-ray source for providing input power to said X-ray source;
X-ray detector for detecting signals from said X-ray source, said X-ray detector being disposed opposite said X-ray source with an object to be examined positioned therebetween;
means for rotating said X-ray source in relation to said object, to cause said X-ray source to transmit X-ray signals through said object and said X-ray detector to detect signals transmitted through said object and to produce output signals representing said transmitted X-ray signals;
means for detecting the relative rotational position of said X-ray source relative to said object;
processing means for taking said output signal from said X-ray detector and producing a tomograph representative thereof, said processing means comprising integrator means for taking said output signals from said X-ray detector and integrating and producing integrated signals, means for converting said integrated signals to digital signals, and means for processing said digital signals and producing a tomograph therefrom; and
control means for controlling said processing means using input signals from said means for detecting the relative rotational position;
the improvement comprising
said power source comprising a single phase transformer having primary winding connectable to an input voltage supply having a selected frequency and secondary winding, rectifier means connected to at least said secondary winding; said rectifier means being also connected to said X-ray source for supplying rectified power of secondary voltage of ripple shape having said selected frequency to said X-ray source to cause emitting of X-ray pulses; and phase locked loop circuit connected between said primary winding and said means for moving, and further connected to said means for detecting relative rotational position, wherein responsive to said selected frequency and said detected relative rotational position, said X-ray source is rotated substantially synchronously in proportion to said selected frequency, and said X-ray source emits at least one X-ray pulse during each cycle of said selected frequency in phase with said rotation of said X-ray source.

8. The system of claim 7, wherein said rectifier means is a half-wave rectifier means.

9. The system of claim 7, wherein said rectifier means is a full wave rectifier means.

10. The system of claim 7, wherein said power source comprises a diode or thyristor and parallel connected resistor, both connected in series to said primary winding.

11. The system of claim 10, wherein said power source comprises a voltage regulator transformer, having primary winding and secondary winding, connected to said primary winding of said transformer and a diode or thyristor and parallel connected resistor, serially connected to said voltage regulator.

12. The system of claim 7, wherein said rectifier means comprises a rectifier and a capacitor connected in series across said secondary winding of said transformer, and wherein said X-ray source is a diode type X-ray tube, having anode electrode connected at a point between said rectifier and said capacitor, and a cathode electrode connected between said rectifier and said secondary winding.

13. The system of claim 7, wherein said X-ray source is a triode type X-ray tube, having an anode, a cathode and grid electrode; and said power source further comprises a phase locked loop means connected to said primary winding, a phase shifter connected to said phase locked loop means, and grid control means connected between said phase shifter and said grid electrode of said X-ray triode tube.

14. The system of claim 7, wherein means are provided for correcting said digitalized signals for zero current error factors.

15. In an X-ray computerized tomograph system comprising an X-ray source;

means for exciting said X-ray source;

X-ray detector means for detecting X-rays transmitted through an object;

means for rotating concurrrently said X-ray source and said X-ray detector means about said object; and means for taking signals from said X-ray detector means and producing computerized tomographs therefrom;

the improvement comprising a single phase transformer having primary winding and secondary winding, said primary winding being connectable to an input voltage supply of selected frequency, and said secondary winding is connected to said X-ray source for supplying secondary voltage at said selected frequency to said X-ray source to excite said X-ray source to emit at least one X-ray pulse during each cycle of excitation;

phase locked loop means connected to said primary winding and to said means for rotating, and responsive to the rotational position of said X-ray source and said X-ray detector means relative to said object, and to the selected frequency of said input source, for causing said means for rotating to rotate said X-ray source and said X-ray detector means substantially synchronously in proportion to said selected frequency; and wherein said input supply performs two concurrent functions, first, to provide excitation for said single phase transformer to generate secondary voltage at said selected frequency to excite said X-ray source to emit at least one X-ray pulse for each cycle of said selected frequency; and, second, to provide a signal based on said selected frequency to cause said phase locked loop means to control the rotation of said X-ray source and said X-ray detector means substantially synchronously in proportion to said selected frequency wherein the emitted X-ray pulse is substantially in phase with said rotation.

* * * * *

UNITED STATES PATENT AND TRADEMARK OFFICE
CERTIFICATE OF CORRECTION

PATENT NO. : 4,532,644
DATED : July 30, 1985
INVENTOR(S) : Keiki Yamaguchi; Tadashi Ogawa; Masayoshi Mitamura; Tooru Shimizu It is certified that error appears in the above—identified patent and that said Letters Patent is hereby corrected as shown below:

Amend Claim 1 as follows line 16 (corresponding to Column 11, line 36), after "X-ray", second occurrence, and before "with" insert --- detector---.

Signed and Sealed this

Eighteenth Day of March 1986

[SEAL]

Attest:

DONALD J. QUIGG

Attesting Officer

Commissioner of Patents and Trademarks